United States Patent [19]

Wollensak et al.

[11] 4,104,255

[45] Aug. 1, 1978

[54] THIOETHER BIS PHENOLIC ANTIOXIDANTS

[75] Inventors: John C. Wollensak; Kju Hi Shin, both of Bloomfield Hills; Kryn G. Ihrman, Farmington, all of Mich.; Paul G. Elsey, Baton Rouge, La.

[73] Assignee: Ethyl Corporation, Richmond, Va.

[21] Appl. No.: 792,645

[22] Filed: May 2, 1977

[51] Int. Cl.$^2$ .................. C08K 5/36; C07C 149/00
[52] U.S. Cl. ........................ 260/45.95 C; 260/609 F
[58] Field of Search ............... 260/609 F, 45.95 B, 260/45.95 C

[56] References Cited

U.S. PATENT DOCUMENTS

| | | | |
|---|---|---|---|
| 3,704,326 | 11/1972 | Song et al. | 260/45.95 C |
| 3,960,758 | 6/1976 | Witte et al. | 260/45.95 C |

OTHER PUBLICATIONS

Plastics Engineering — Oct., 1976, pp. 51–57.

*Primary Examiner*—V. P. Hoke
*Attorney, Agent, or Firm*—Donald L. Johnson; Robert A. Linn; Joseph D. Odenweller

[57] ABSTRACT

Ortho-cyclopentyl-hydroxybenzyl sulfides (e.g. di-(3,5-dicyclopentyl-4-hydroxybenzyl)sulfide) are effective antioxidants.

3 Claims, No Drawings

THIOETHER BIS PHENOLIC ANTIOXIDANTS

BACKGROUND

Various substituted hydroxybenzyl sulfides have been disclosed to be antioxidants (U.S. Pat. No. 3,274,258; U.S. Pat. No. 3,272,869).

SUMMARY

According to the present invention novel antioxidant compounds are provided which are hydroxybenzyl sulfides having at least one cyclopentyl group ortho to the phenolic hydroxyl group. Such cyclopentyl substituted compounds have been found to possess superior antioxidant properties compared to several commercial antioxidants.

DESCRIPTION OF THE PREFERRED EMBODIMENTS

A preferred embodiment of the invention is a compound having the formula:

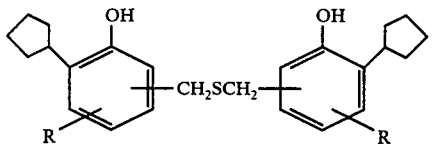

wherein each R is independently selected from the group consisting of cyclopentyl and alkyl groups containing 1–12 carbon atoms and is bonded to the phenolic benzene ring at a position ortho or para with respect to the phenolic hydroxyl group, the —CH$_2$SCH$_2$— bridge being bonded between the remaining ortho or para position of the phenolic benzene rings.

Examples of such compounds are:
di-(2-hydroxy-3-cyclopentyl-5-methylbenzyl)sulfide
di-(2-hydroxy-3-cyclopentyl-5-tert-butylbenzyl)sulfide
di-(2-hydroxy-3,5-dicyclopentylbenzyl)sulfide
di-(2-hydroxy-3-cyclopentyl-5-n-dodecylbenzyl)sulfide
2,4'-dihydroxy-3,3'-dicyclopentyl-5-isopropyl-5'-sec-butyl dibenzyl sulfide
2,4'-di-hydroxy-3,3',5,5'-tetra-cyclopentyl dibenzyl sulfide
3,3'-di-cyclopentyl-4,4'-di-hydroxy-5-methyl-5'-tert-butyl dibenzyl sulfide
di-(3-cyclopentyl-4-hydroxy-5-tert-butylbenzyl)sulfide
di-(3-cyclopentyl-4-hydroxy-5-n-dodecylbenzyl)sulfide
di-(3-cyclopentyl-4-hydroxy-5-tert-octylbenzyl)sulfide In a more preferred embodiment both phenolic substituents in formula I are cyclopentyl. These compounds are exemplified by di-(2-hydroxy-3,5-dicyclopentylbenzyl)sulfide, di(3,5-dicyclopentyl-4-hydroxybenzyl)sulfide and 2,4'-di-hydroxy-3,3',5,5'-tetra-cyclopentyl dibenzyl sulfide.

In a still more preferred embodiment the phenolic groups are bridged at their para position. This embodiment can be represented by the following formula:

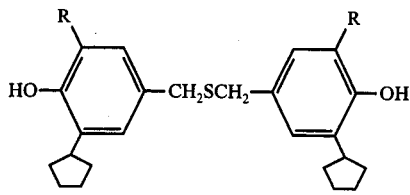

in which R is the same as in formula I.

These compounds are exemplified by:
di-(3-cyclopentyl-4-hydroxy-5-methylbenzyl)sulfide
di-(3-cyclopentyl-4-hydroxy-5-isopropylbenzyl)sulfide
di-(3-cyclopentyl-4-hydroxy-5-tert-butylbenzyl)sulfide
di-(3-cyclopentyl-4-hydroxy-5-sec-butylbenzyl)sulfide
di-(3-cyclopentyl-4-hydroxy-5-tert-octylbenzyl)sulfide
di-(3-cyclopentyl-4-hydroxy-5-sec-dodecylbenzyl)sulfide
di-(3,5-dicyclopentyl-4-hydroxybenzyl)sulfide The most preferred embodiment is represented by formula II in which R is cyclopentyl. This compound is di-(3,5-dicyclopentyl-4-hydroxybenzyl)sulfide.

The compounds can be made by reacting (1) a phenol of the following formula:

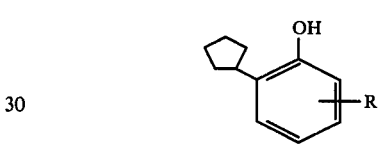

in which R is cyclopentyl or a C$_{1-12}$ alkyl and is bonded at the ortho or para position with (2) formaldehyde and (3) sodium sulfide in a suitable reaction medium. Such procedures are described by U.S. Pat. No. 2,736,703 and U.S. Pat. No. 3,272,869.

Alternatively the compound can be made by converting the above phenol to the corresponding chloromethyl derivative by reaction with formaldehyde and HCl (as described in U.S. Pat. No. 3,257,321) and reacting this intermediate with Na$_2$S as described in U.S. Pat. No. 3,065,275. For the sake of brevity, the above patents showing how to make the present compounds are incorporated herein by reference. The appropriate ortho-cyclopentyl compound of formula III is substituted for the starting reactants shown in these patents.

The following example serves to illustrate the manner of making the present compounds.

EXAMPLE 1

In a reaction vessel was placed 300 ml methanol, 100 g of 2,6-di-cyclopentylphenol, 6.2 g Na$_2$S·9 H$_2$O and 38.5 ml 37% aq. formaldehyde. The mixture was stirred under nitrogen and refluxed for 1.25 hours. The methanol was then distilled out under vacuum and 200 ml dioxane added. The dioxane was then distilled out under vacuum and 500 ml benzene added to dissolve the product. The benzene solution was filtered to remove inorganics, washed with water and then dried over anhydrous CaSO$_4$. The benzene was then distilled out under vacuum and the residue recrystallized from pet. ether. The product obtained was recrystallized from isopropanol to give 19 g of di(3,5-dicyclopentyl-4-hydroxybenzyl)sulfide, mp 149°–150° C. It analyzed 79.37% C, 9.23% H and 6.14% S. Structure was confirmed by NMR.

Other compounds of the invention can be made in similar manner by substituting other ortho-cyclopentylphenols for the 2,6-dicyclopentylphenol used in Example 1. Use of 2-cyclopentyl-6-tert-butylphenol will give di-(3-cyclopentyl-4-hydroxy-5-tert-butylbenzyl)sulfide. Likewise, use of 2,4-dicyclopentylphenol will give di-(2-hydroxy-3,5-dicyclopentylbenzyl)sulfide. Use of mixtures such as mixtures of 2,6-dicyclopentylphenol and 2,4-dicyclopentylphenol will give a mixture of product containing di-(3,5-dicyclopentyl-4-hydroxybenzyl)sulfide, di-(2-hydroxy-3,5-dicyclopentylbenzyl)sulfide and 2,4'-dihydroxy-3,3',5,5'-tetra-cyclopentyl dibenzylsulfide.

The antioxidants are added to the substrate to be protected in a small but effective amount sufficient to give the required degree of antioxidant protection. This can vary widely within the range of about 0.005–10 weight percent. A preferred range is about 0.05–5 weight percent. Good results are usually achieved using about 0.01–3 weight percent.

The antioxidant can be used in a broad range of organic material normally subject to gradual degradation in the presence of oxygen during use over an extended period. In other words, the organic compositions protected by the present antioxidants are the type in which the art recognizes the need for antioxidant protection and to which an antioxidant of some type is customarily added to obtain an extended service life. The oxidative degradation protected against is the slow gradual deterioration of the organic composition rather than, for example, combustion. In other words, the present additives are not flame retarding additives nor flame suppressing additives and the degradation protected against is not combustion but, rather, the gradual deterioration of the organic composition due to the effects of oxygen over an extended period of time.

Examples of organic materials in which the additives are useful include polymers, both homopolymers and copolymers, of olefinically unsaturated monomers, for example, polyolefins such as polyethylene, polypropylene, polybutadiene, and the like. Also, poly-halohydrocarbons such as polyvinyl chloride, polychloroprene, polyvinylidene chloride, polyfluoro olefins, and the like, are afforded stabilization. The additives provide antioxidant protection in natural and synthetic rubbers such as copolymers of olefinically unsaturated monomers including styrene-butadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylenevinyl acetate copolymers are protected, as are butene-methylacrylate copolymers. Nitrogen-containing polymers such as polyurethanes, nitrile rubber, and lauryl acrylate-vinyl-pyrrolidone copolymers are effectively stabilized. Adhesive compositions such as solutions of polychloroprene (neoprene) in toluene are protected.

Fats and oils of animal and vegetable origin are protected against gradual deterioration. Examples of these are lard, beef tallow, coconut oil, safflower oil, castor oil, babassu oil, cottonseed oil, corn oil, rapeseed oil, tall oil and the like.

Petroleum oils and waxes such as solvent-refined, midcontinent lubricating oil, microcrystalline wax, and Gulfcoast lubricating oils are effectively stabilized.

Animal feeds such as ground corn, cracked wheat, oats, wheat germ, alfalfa, and the like, are protected by mixing a small but effective amount of the present additive with these products. Vitamin extracts, especially the fat-soluble vitamins such as Vitamins A, B, D, E and C, are effectively stabilized against degradation.

The additives are useful in foamed plastics such as expanded polystyrene, polyurethane foams, and the various foamed rubbers, alkyd resins such as short oil terephthalic acid-glycerol-linseed oil resins, and typical long oil resins of trimellitic acid-glycol-tung oil resins including epoxide-modified alkyl resins. Epoxy resins themselves such as isopropylidenebisphenolepichlorohydrin epoxy resins are stabilized against degradation.

Hydrocarbons such as gasoline, kerosene, diesel fuel, fuel oil, furnace oil, and jet fuel are effectively protected. Likewise, synthetic hydrocarbon lubricants, for example, $\alpha$-decene trimer, polybutene lubricants, di- and tri-$C_{12-30}$ alkylated benzene and naphthalene synthetic lubricants are likewise protected.

Organometallics such as tetraethyllleated, tetramethyllead, tetravinyllead, ferrocene, methyl ferrocene, cyclopentadienyl manganese tricarbonyl, methyl cyclopentadieneyl manganese tricarbonyl, cyclopentadienyl nickel nitrosyl, and the like, are effectively protected against oxidative degradation. Silicone oils and greases are also protected.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethyleneglycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and other polyformaldehydes are also protected.

Linear polyesters such as phthalic anhydride-glycol condensates are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The additives can be used to protect any of the many organic substrates to which an antioxidant is normally added. It can be used where economics permit to protect such substrates as asphalt, paper, fluorocarbons such as teflon, polyvinyl acetate, polyvinylidene chloride, coumarone-indene resins, polyvinyl ethers, polyvinylidene bromide, polyvinyl bromide, acrylonitrile, vinyl bromide copolymer, vinyl butyral resins, silicones such as dimethylsilicone lubricants, phosphate lubricants such as tricresylphosphate, and the like.

The additives are incorporated into the organic substrate in a small but effective amount so as to provide the required antioxidant protection. A useful range is from about 0.005 to about 10 weight percent, and a preferred range is from about 0.05 to 5 weight percent.

Methods of incorporating the additive into the substrate are well known. For example, if the substrate is liquid the additive can be merely mixed into the substrate. Frequently the organic substrate is in solution and the additive is added to the solution and the solvent removed. Solid organic substrates can be merely sprayed with a solution of the additive in a volatile solvent. For example, stabilized grain products result from spraying the grain with a toluene solution of the additive. In the case of rubbery polymers the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized. The following will serve to illustrate the manner in which the additives are blended with various organic substrates. The following described organic compositions containing the additives of the present invention. Additives are designated as follows:

A — di-(3,5-di-cyclopentyl-4-hydroxybenzyl)sulfide
B — di-(3-cyclopentyl-5-tert-butyl-4-hydroxybenzyl)sulfide
C — di-(3,5-dicyclopentyl-2-hydroxybenzyl)sulfide
D — di-(3-cyclopentyl-5-methyl-4-hydroxybenzyl)sulfide
E — di-(3-cyclopentyl-5-tert-octyl-4-hydroxybenzyl)sulfide
F — di-(3-cyclopentyl-5-sec-dodecyl-4-hydroxybenzyl)sulfide
G — 2,4'-di-hydroxy-3,3',5,5'-tetra-cyclopentyl dibenzylsulfide
H — di-(3-cyclopentyl-5-isopropyl-4-hydroxybenzyl)sulfide
I — di-(3,5-dicyclopentyl-4-hydroxybenzyl)sulfide
J — di-(3-cyclopentyl-5-tert-decyl-4-hydroxybenzyl)sulfide
K — 2,4'-di-hydroxy-3,3'-di-cyclopentyl-5,5'-di-tert-butyl dibenzyl sulfide
L — di-(3,5-dicyclopentyl-4-hydroxybenzyl)sulfide
M — di-(3-cyclopentyl-5-methyl-2-hydroxybenzyl)sulfide
N — di-(3,5-dicyclopentyl-4-hydroxybenzyl)sulfide

EXAMPLE 2

To a synthetic rubber master batch comprising 100 parts of SBR rubber having an average molecular weight of 60,000, 50 parts of mixed zinc propionate stearate, 50 parts carbon black, 5 parts road tar, 2 parts sulfur and 1.5 parts of mercapto benzothiazole is added 1.5 partsof additive A. After mastication, the resultant master batch is cured for 60 minutes using 45 psi steam pressure, resulting in a stabilized SBR vulcanizate.

EXAMPLE 3

A synthetic SBR polymer is prepared by polymerizing 60 percent styrene and 40 percent butadiene in an aqueous emulsion employing a sodium oleate emulsifier and a peroxide catalyst. Following this, sufficient additive B is added to produce 0.3 weight percent, based upon the SBR polymer. The emulsion is then coagulated using an acidified salt solution and the coagulated polymer compressed into bales for storage. The polymer is stable during storage and can later be compounded to prepare SBR vulcanizates.

EXAMPLE 4

One part of additive C is blended with 100 parts of raw butyl rubber prepared by the copolymerization of 90 percent isobutylene and 10 percent isoprene, resulting in a stable elastomer.

EXAMPLE 5

A cis-polybutadiene polymer is prepared having 90 percent cis configuration by polymerizing butadiene in a toluene solvent employing a diethyl aluminum chloride-cobalt iodide catalyst. Following the polymerization, a small amount sufficient to provide 0.2 weight percent of additive D is added to the toluene solution, following which the solution is injected into boiling water together with steam causing the solvent to distill out and the cis-polybutadiene to coagulate, forming a rubber crumb. The crumb is dried and compressed into bales, resulting in a stabilized cis-polybutadiene.

EXAMPLE 6

A butadiene-acrylonitrile copolymer is prepared from 1,3-butadiene and 32 percent of acrylonitrile. One percent, based on the weight of polymer, of additive E is added as an emulsion in a sodium oleate solution. The latex is coagulated and the coagulum is washed and dried, resulting in a stabilized butadiene-acrylonitrile copolymer.

EXAMPLE 7

To 1,000 parts of a solid polypropylene powder is added 5 parts of additive F and 10 parts of dilaurylthiodipropionate. The mixture is heated to its melting point and rapidly stirred and extruded to form a useful polypropylene filament.

EXAMPLE 8

To 1,000 parts of polyethylene is added 3 parts of additive G and 5 parts of dilaurylthiodipropionate. The mixture is heated to its melting point and stirred and then passed through an extruder having a central mandrel to form tubular polyethylene which is inflated to form a useful polyethylene film.

EXAMPLE 9

To 100,000 parts of a midcontinent, solvent-refined, mineral oil having viscosity of 100° F. of 373.8 SUS and at 210° F. of 58.4 SUS is added 500 parts of additive H. Following this is added 100 parts of a zinc dialkyldithiophosphate, 50 parts of an overbased calcium alkaryl sulfonate, 1,000 parts of a polydodecylmethacrylate V.I. improver and 2,000 parts of a 70 percent active oil solution of an alkenyl succinimide of tetraethylenepentamine in which the alkenyl group has a molecular weight of 950. The resultant mixture is blended while warm, following which it is filtered and packaged, giving a stable lubricating oil useful in automotive engines.

EXAMPLE 10

To 10,000 parts of a dimethyl silicone lubricating oil is added 50 parts of additive I. The mixture is stirred at 50° C. until thoroughly blended, resulting in a stable silicone lubricating oil.

EXAMPLE 11

To 10,000 parts of corn oil is aded 15 parts of additive A. The mixture is stirred, giving a corn oil highly resistant to normal oxidative degradation.

EXAMPLE 12

To 10,000 parts of trimethylolpropane tripelargonate is added 200 parts of tricresylphosphate, 10 parts of dimethyl silicone, 10 parts of benzothiazole, 50 parts of phenyl-β-naphthyl amine, and 50 parts of additive J, resulting in a stabilized synthetic ester lubricant.

EXAMPLE 13

Wax paper is made by impregnating paper with paraffin wax containing 0.05 weight percent of a mixture of additive K. The wax paper is used to make containers for potato chips which results in chips having extended shelf life.

EXAMPLE 14

To 10,000 parts of gasoline having an 87 R.O.N. is added 20 parts of additive L and sufficient commercial tetraethyllead antiknock fluid to provide 2.5 grams of lead per gallon, resulting in a stabilized gasoline having a 96 R.O.N.

EXAMPLE 15

To 10,000 parts of 41 cetane diesel fuel is added 50 parts of hexyl nitrate and 25 parts of additive M, providing a stable diesel fuel.

EXAMPLE 16

To 10,000 parts of melted lard is added 10 parts of additive N and the mixture is stirred until thoroughly blended resulting in a lard highly resistant to normal oxidative degradation.

From the foregoing, it is apparent how to prepare stable organic compositions using the additives of this invention.

The antioxidants of this inventon may be used alone as the sole antioxidant or may be used in combination with other antioxidants or compounds which synergistically affect the effectiveness of the antioxidant. Examples of other antioxidants include 4,4′methylenebis(2,6-di-tert-butylphenol), 1,3,5-trimethyl-2,4,6-tri(3,5-di-tert-butyl-4-hydroxybenzyl)benzene, 2,6-dicyclopentyl-4-methylphenol, 4,4′-thiobis(6-tert-butyl-m-cresol), 4,4′-butylidenebis(6-tert-butyl-m-cresol) β-(3,5-di-tert-butyl-4-hydroxy phenyl) propionic acid pentaerythritol ester and the like.

Particularly preferred synergists are the dialkyl-thio-diproprionates such as dilauryl-thio-dipropionate and distearyl-thio-dipropionate. Such synergists are particularly effective in polyolefin (e.g., polypropylene) composition and are used in concentrations of about 0.65 to about 0.3 weight percent.

Other synergists are dialkyl phosphites (e.g., dibutylphosphite, trialyl phosphites, trialkyl phosphites (e.g., tributylphosphite), dialkyl tin sulfides (e.g., dibutyl tin sulfides) and the like.

Tests have been conducted which demonstrates the effectiveness of the present antioxidants.

Tests were carried out to demonstrate the antioxidant properties of the additive. For comparison two well-known commercial antioxidants were included in the test. In these tests 25 mil sheets of polypropylene were molded containing the additives. Five replicates of each are inclined. They are aged in an oven at 150° C. Failure is indicated by cracking, crazing or powdering on the surface of 3 of the 5 replicates.

One non-additive blank was included as well as one containing a dilauryl thiodipropionate (DLTDP) synergist. In addition, several commercial antioxidants were included for comparison. The results were as follows:

|   | Additive | Conc. (Wt %) | Hours to Failure |
|---|---|---|---|
| 1. | blank | — | 3 |
| 2. | di-(3,5-di-cyclo-pentyl-4-hydroxy-benzyl)sulfide | 0.1 | 456 |
| 3. | " | 0.1 | |
|   | plus DLTDP | 0.2 | 900 + |
| 4. | n-octadecyl β-(3,5-di-tert-butyl-4-hydroxyphenyl)-propionate | 0.1 | 250 |
| 5. | tris-(3-methyl-6-tert-butylphenol)-butane | 0.1 | 120 |

The "+" sign indicates the sample had not yet failed.

As the above results show the new additives are very effective antioxidants and respond well to synergists.

We claim:
1. An antioxidant compound namely di-(3,5-dicyclopentyl-4-hydroxybenzyl)sulfide.
2. A polyolefin normally subject to gradual degradation due to oxidation containing an antioxidant amount of the antioxidant compound of claim 1.
3. A composition of claim 2 wherein said polymer is polypropylene.

* * * * *

UNITED STATES PATENT AND TRADEMARK OFFICE
CERTIFICATE OF CORRECTION

PATENT NO. : 4,104,255
DATED : August 1, 1978
INVENTOR(S) : John C. Wollensak et al It is certified that error appears in the above-identified patent and that said Letters Patent are hereby corrected as shown below:

Column 8. line 11, "0.65" should read -- 0.05 --.

Signed and Sealed this

Sixteenth Day of January 1979

[SEAL]

Attest:

RUTH C. MASON
Attesting Officer

DONALD W. BANNER
Commissioner of Patents and Trademarks